(12) United States Patent
Starkey

(10) Patent No.: US 9,016,744 B2
(45) Date of Patent: Apr. 28, 2015

(54) MECHANICAL CAPSTAN AMPLIFIER

(75) Inventor: Michael Starkey, Charlotte, NC (US)

(73) Assignee: Ohio University, Athens, OH (US)

( * ) Notice: Subject to any disclaimer, the term of this patent is extended or adjusted under 35 U.S.C. 154(b) by 208 days.

(21) Appl. No.: 13/697,931

(22) PCT Filed: May 20, 2011

(86) PCT No.: PCT/US2011/037303
§ 371 (c)(1),
(2), (4) Date: Jan. 3, 2013

(87) PCT Pub. No.: WO2011/146815
PCT Pub. Date: Nov. 24, 2011

(65) Prior Publication Data
US 2013/0131815 A1 May 23, 2013

Related U.S. Application Data

(60) Provisional application No. 61/346,534, filed on May 20, 2010.

(51) Int. Cl.
*A61F 2/58* (2006.01)
*B25J 15/10* (2006.01)
*A61F 2/30* (2006.01)
*B65H 59/00* (2006.01)
*A61F 2/68* (2006.01)
*A61F 2/50* (2006.01)
*A61F 2/70* (2006.01)

(52) U.S. Cl.
CPC . *A61F 2/30* (2013.01); *A61F 2/583* (2013.01); *A61F 2/68* (2013.01); *A61F 2002/5093* (2013.01); *A61F 2002/701* (2013.01); *B65H 59/00* (2013.01); *Y10S 901/21* (2013.01); *Y10S 901/38* (2013.01)

(58) Field of Classification Search
USPC .............. 294/106, 111, 86.4; 901/21, 36, 38; 623/62, 64, 24
See application file for complete search history.

(56) References Cited

U.S. PATENT DOCUMENTS

| 2,549,074 | A | * | 4/1951 | Fishbein et al. | ................ 623/64 |
| 2,549,716 | A | * | 4/1951 | Simpson | ......................... 623/64 |
| 3,413,658 | A | * | 12/1968 | Becker | ............................ 623/64 |
| 4,364,593 | A | * | 12/1982 | Maeda | ......................... 294/106 |

(Continued)

OTHER PUBLICATIONS

International Preliminary Report on Patentability in corresponding International Patent Application PCT/US2011/037303, filed May 20, 2011.

(Continued)

*Primary Examiner* — Paul T Chin
(74) *Attorney, Agent, or Firm* — Wood, Herron & Evans, LLP

(57) ABSTRACT

A mechanical capstan amplifier. The mechanical capstan amplifier (60) having a first tensioner (64) with a first actuating rod (72) extending therefrom. The first tensioner (64) is configured to rotate the first actuating rod (72). The amplifier (60) also includes a drive motor (62) having a drive rod (78) extending therefrom. The drive motor (62) is configured to rotate the drive rod (78). A first cord (66), extending between the first actuating rod (72) and a first load to be moved also extends at least partially around the drive rod (78). Actuation of the first tensioner (64) causes the first cord (66) to tighten around the drive rod (78) and moves the load.

17 Claims, 3 Drawing Sheets

(56) References Cited

U.S. PATENT DOCUMENTS

| | | | |
|---|---|---|---|
| 4,685,929 A * | 8/1987 | Monestier | 623/64 |
| 4,921,293 A * | 5/1990 | Ruoff et al. | 294/111 |
| 5,092,646 A * | 3/1992 | Smallridge | 294/111 |
| 6,913,627 B2 * | 7/2005 | Matsuda | 623/64 |
| 7,222,904 B2 * | 5/2007 | Matsuda | 294/111 |
| 8,297,672 B2 * | 10/2012 | Kim et al. | 294/106 |
| 8,641,114 B2 * | 2/2014 | Kurita et al. | 294/106 |

OTHER PUBLICATIONS

United States Patent and Trademark Office; Search Report and Written Opinion in International Application No. PCT/US2011/037303 dated Sep. 8, 2011; 11 pages.

* cited by examiner

MECHANICAL CAPSTAN AMPLIFIER

FIELD OF THE INVENTION

The present invention relates generally to mechanical amplifiers.

BACKGROUND OF THE INVENTION

Since the inception of the field of robotics, robotic designers have attempted to mimic biological systems. However, the realization of this goal has been impaired by the complexity of biological systems. More specifically, biological organisms have developed many adaptations over evolutionary timeframes. For example, the driving force of some types of biological movement, the muscle, is a highly developed mechanical system that is configured to generate high forces, contract at high velocities, and use relatively low amounts of energy.

In vertebrate motion, the muscles are coupled to skeletal elements via tendons. Movement is produced by the contraction of the muscle tissue, which thereby pulls one skeletal element toward another skeletal element; a second muscle tissue is required to reverse the movement. One type of known biomimetic robots employs anatomical-style joints with cable actuated linkages that replicate muscle; however, these joints are difficult to control and require highly complex mathematical simulation. Therefore, directly driven linkages are used to simplify control of the robot and the mathematical simulations.

Yet, one of the greatest challenges to robotic designers is to develop a mechanism that accurately and mathematically replicates vertebrate muscle by providing high levels of force within the space and mass limitations of a typical vertebrate joint. In some embodiments, designers tether the robot to a power source. This is undesirable for at least the reason that it limits the robot's mobility. Alternatively, a limited power supply may be placed on-board the robot and may include batteries; however, batteries add large amounts of weight to the robot and require still more energy to power the robot.

To overcome the weight issue, robotic designers have attempted to under actuate movements, e.g., provide fewer motors than there are degrees of freedom ("DOF") in a replicated joint system. The missing DOFs are then actuated through passive mechanisms, such as through the inclusion of springs. One such example is a biomimetic hand, which attempts to replicate the human hand's over 20 DOFs all contained within a relatively small volume. Known solutions for the biomimetic hand have included integrating micro motors with large gearing ratios into fingers of robotic hands. But these solutions have not provided satisfactory levels of force within the permitted space. Still further, this method again sacrifices control and oversimplifies the joint system.

Capstans are known to utilize friction in order to amplify work output. According to the conventional theory, capstans were believed to operate in accordance with:

$T_2 = T_1 e^{\mu\beta}$ where $T_2$ is the force derived from operating the capstan system, $T_1$ is the force that is input into the capstan system, $\mu$ is the coefficient of friction of the cord, and $\beta$ is the angle of contact (measured in radians) formed by the cord at the capstan. However, this conventional equation supposes that a constant friction input into the capstan system at a given angle of contact will amplify at a constant rate. Capstans generally operate by creating friction between the cord 66 and the drive rod 78. After a load is coupled to the load bearing end 68 of the cord 66, the opposing, actuating end 70 is pulled by winding the cord 66 around the tensioning rod 72 and friction develops between the cord 66 and the drive rod 78 (i.e., the capstan). This friction transfers a portion of the force needed to move the load from the tensioning rod 72 to the drive rod 78. An understanding of capstan operation may be beneficial in various applications, such as in robotics.

Thus, there remains a need for a mechanical system that is capable of producing the forces and speeds of biological organisms while minimizing the mechanical system's weight, volume, and power consumption.

SUMMARY OF THE INVENTION

The present invention overcomes the foregoing problems and other shortcomings, drawbacks, and challenges of known conventional biomimetic actuation devices. While the invention will be described in connection with certain embodiments, it will be understood that the invention is not limited to these embodiments. To the contrary, this invention includes all alternatives, modifications, and equivalents as may be included within the spirit and scope of the present invention.

In accordance with one embodiment of the invention, a mechanical capstan amplifier is described. The mechanical capstan amplifier has a first tensioner with a first actuating rod extending therefrom. The first tensioner is configured to rotate the first actuating rod. The amplifier also includes a drive motor having a drive rod extending therefrom. The drive motor is configured to rotate the drive rod. A first cord, extending between the first actuating rod and a first load to be moved extends at least partially around the drive rod. In its normal state, the first cord fits loosely around the drive rod so that the drive rod can rotate without moving the first cord.

The first motor or other tensioner, when activated, pulls the first cord tighter causing it to engage the drive rod. At this point, there is sufficient friction between the drive rod and the first cord to allow the drive rod to pull the first cord. When the first motor reverses, the tension on the first cord is released and the drive rod will no longer pull the first cord.

Another embodiment of the mechanical capstan amplifier includes a first tensioner and a second tensioner, each coupled respectively to a first actuating rod and a second actuating rod. The tensioners are configured to rotate the respectively coupled actuating rod. The amplifier also includes a drive motor having a drive rod extending therefrom. The drive motor is configured to rotate the drive rod. A first cord extending between the first actuating rod and a first load to be moved also extends at least partially around the drive rod. A second cord extends between the second actuating rod and a second load to be moved. The second cord also extends at least partially around the drive rod at a position on the drive rod that is different from the position of the first cord. Thus, one or more powerful tensioners may be used to tighten two or more cords with respect to the drive rod, thereby reducing the number of tensioners required to move a load.

In accordance with another embodiment of the invention, a biomimetic joint is described. The biomimetic joint includes a first skeletal element rotationally coupled to a second skeletal element and a mechanical capstan amplifier that is configured to move the first skeletal element relative to the second skeletal element. The mechanical capstan amplifier includes a first tensioner with a first actuating rod extending therefrom. The first motor is configured to rotate the first actuating rod. The amplifier also includes a drive motor having a drive rod extending therefrom. The drive motor is configured to rotate the drive rod. A first cord extends from the first actuating rod to the first skeletal element and also at least partially around the drive rod. Actuating the tensioner causes the first cord to tighten with respect to the drive rod, which then allows the drive rod to pull the first cord and move the first skeletal element.

A method of moving a first load is also described. The method includes providing a first cord that extends at least partially around a drive rod and to the first load. The drive rod may rotate as the first cord is loosely coupled thereto. When the first cord is tightened with respect to the drive rod, rotation of the drive rod creates friction between the drive rod and the first cord. Continued friction causes the drive rod to pull the first cord and move the first load.

The above and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention and, together with a general description of the invention given above, and the detailed description of the embodiments given below, serve to explain the principles of the invention.

DETAIL DESCRIPTION

The present invention is described in the context of a biomimetric hand. This invention can also be employed in many other environments unrelated to biomimetrics. It may be applied to a wide variety of different applications. It can be miniaturized or enlarged depending on the application.

Figure 1:
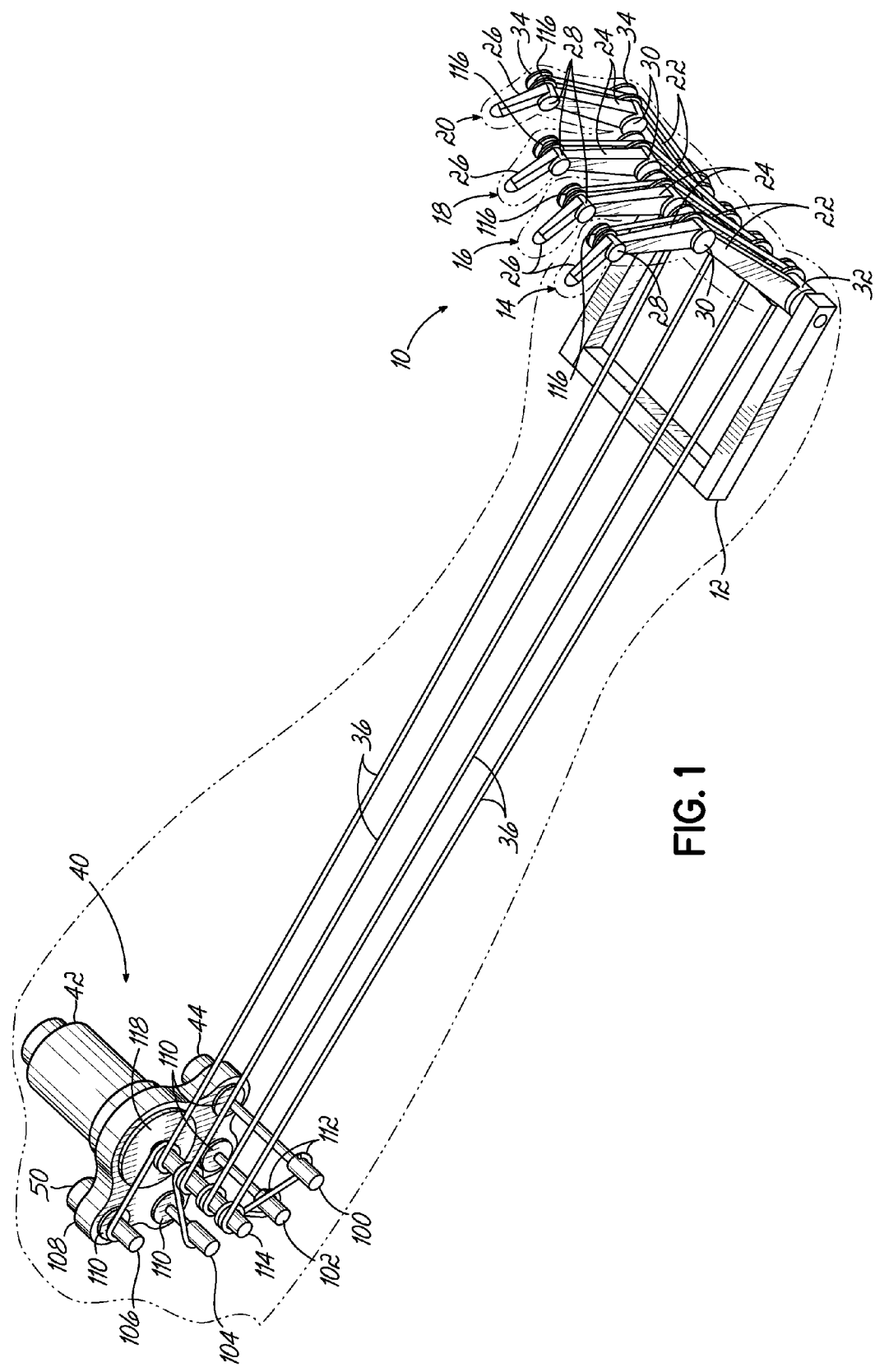
FIG. 1 is a perspective view of a biomimetic hand joint system using a mechanical capstan amplifier in accordance with one embodiment of the invention.

Turning now to the figures, and in particular to FIG. 1, a biomimetic hand 10 is shown and generally includes a palm portion 12 supporting four fingers 14, 16, 18, 20 extending distally therefrom. Each finger 14, 16, 18, 20 includes a proximal phalange 22, a medial phalange 24, and a distal phalange 26, wherein a distal joint 28 couples each distal phalange 26 to the respective medial phalange 22, a medial joint 30 couples each medial phalange 24 to the respective proximal phalange 22, and the proximal phalanges 22 are rotatably coupled to a distal rod 32 of the palm portion 12.

Each of the distal and medial joints 26, 28 and the joints formed at the distal rod 32 includes a knob 34, which, as shown, is positioned lateral to the respective joint; however, the knob 34 could be incorporated into the joint itself if so desired. Each knob 34 is configured to receive a cord 36 such that the cord is coupled to the knob 34 of each distal joint 28, extends along the knobs 34 of each medial joint 30 and at the distal rod 32, and further extends proximally along and away from the palm portion 12 to a mechanical capstan amplifier 40, one embodiment being shown in FIG. 1. Accordingly, each finger 14, 16, 18, 20 presents a load that is rendered moveable by actuating the mechanical capstan amplifier 40 in a manner that is described in greater detail below.

The biomimetic hand 10, as illustrated, is analogous to a cable tendon robot, wherein full control of a joint within the cable tendon robot may include two motors in order to actuate the antagonist tendons (or, as illustrated, the cords 36). However, the mechanical capstan amplifier 40 replaces the two requisite motors with a combination of a single large driving motor 42 and a plurality of smaller tensioning, or control motors 44, 46, 48, 50 corresponding with fingers 14, 16, 18, 20, respectively.

Figure 2:
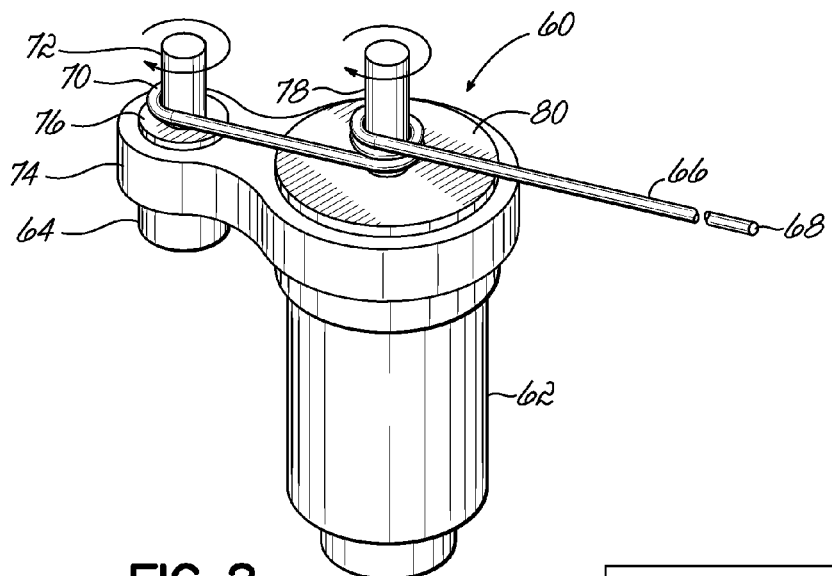
FIG. 2 is a perspective view of a mechanical capstan amplifier in accordance with another embodiment of the invention.

FIG. 2 illustrates the basic principle of the present invention. Mechanical capstan amplifier 60 has a single driving motor 62 and a single control motor 64. The illustrated embodiment includes a cord 66 having a load bearing end 68 and an actuating end 70. The actuating end 70 is coupled to a tension rod 72, which is supporting by a housing 74 and operationally coupled to the control motor 64. The tensioning rod 72 may be any rigid metallic or polymeric material, such as high-density polyethylene ("HDPE"). A washer 76 may be positioned between the tensioning rod 72 and the housing 74 to reduce undesired friction, if desired. The control motor 64 may be an electric motor, a stepper motor, a servo motor, or other similar motor that is capable of rotating the tensioning rod 72 to wind the cord 66. It can be any mechanism that allows the cord 66 to be pulled slightly to tighten around the drive rod thus it can be a spring mechanism, a solenoid type device, a pusher which engages the cord 66, or any other such tensioner. While not specifically shown, the tensioning rod 72 may include a concave shaped that is configured to receive and retain the cord 66 in position on the tensioning rod 72.

The cord 66 may be any unitary or woven material comprised of naturally-occurring or synthetic materials. Alternatively, belts, straps, chains, cables, or bands may also be used. Exemplary materials may include, for example, nylon, polypropylene, natural fibers such as hemp or cotton, or various metals.

The cord 66 extends away from the tensioning rod 72 and extends at least partially around a drive rod 78. The drive rod 78 is also supported by the housing 74, is operably coupled to the drive motor 62, and may include a washer 80 to reduce undesired friction while the drive rod 78 is rotating. The drive rod 78 may be constructed in a manner that is similar to the tensioning rod 72 or of a different material, with or without a concave structure to retain the cord 66, as was described above. The drive motor 62 may also be an electric motor, a stepper motor, a servo motor, or other similar motor but is generally larger than the control motor 64.

As shown in FIG. 2, the cord 66 forms a 540° angle about the drive rod 78. Said another way, the cord 66 is wrapped one and one half times around the drive rod 78; however, this angle should not be considered to be limiting. Instead, multiple angles are described below and would fall within the spirit of the invention.

Instead, and while not wishing to be bound by theory, Applicant believes that two transient influences lead to non-linear amplification of the tension output by the mechanical capstan amplifier. That is, Applicant has found that the tension undergoes an initial rapid amplification that is followed with a slow exponential decay with further input tension. The force, $T_2$, derived from the mechanical capstan amplifier may be more accurately described:

$$T_2 = T_1(-N_d e^{-\lambda_d x} + N_0 e^{-\lambda x} + SS)$$

where $T_1$ is the force input into the capstan system, $N_d$ is the magnitude of fast rising exponential, $\lambda_d$ is the rate of exponential increase, $N_0$ is the magnitude of the slow decay exponential, $\lambda$ is the rate of exponential decay, and $SS$ is the steady state.

Figure 2A:
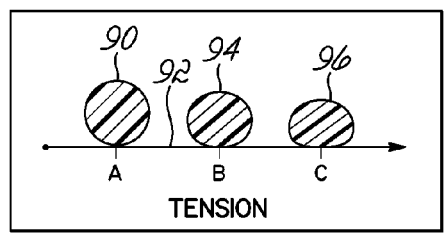
FIG. 2A is a cross-sectional view of increased tension applied to a cord with respect to a surface.

Although not bounded by any particular theory, the initial exponential increase, indicated by the value of $\lambda_d$, is believed to occur as the cord conforms to the surface of the capstan. For example, in FIG. 2A a first cord 90 at position A, having little to no tension applied thereto, has a substantially circular cross-section. In other words, the first cord 90 only tangentially contacts the surface 92, which represents the capstan. As the user operates the capstan, the tension increases quickly and, as shown by a second cord 94 at position B, the second cord 94 becomes more oval in shape and begins to flatten along the surface 92. The flattening may continue, such as shown by the third cord 96 at position C, until a critical tension is achieved and related to rate of exponential increase. Then, the slow exponential loss of diminishing returns, associated with $\lambda$, and dictates the behavior of the capstan system.

Figure 3:
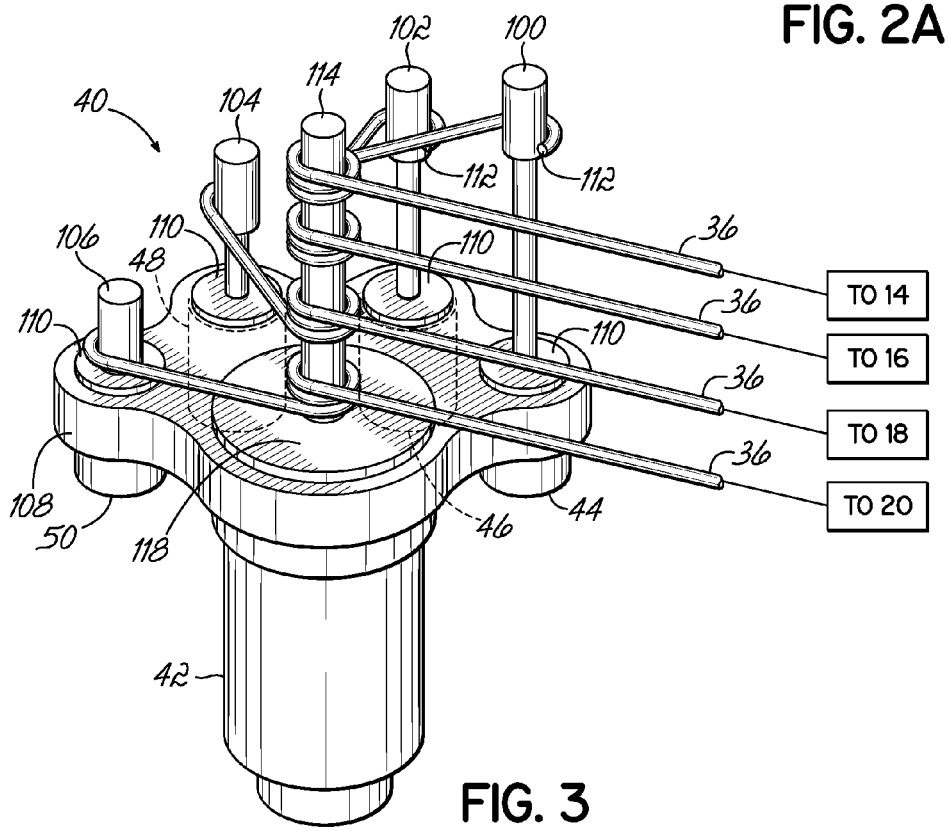
FIG. 3 is a perspective view of the mechanical capstan amplifier of FIG. 1.
Figure 4:
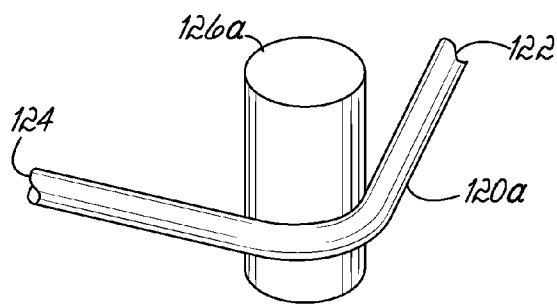
FIGS. 4-8 are perspective views of angles of contact for use with the drive rod of a mechanical capstan amplifier in accordance with various embodiments of the invention.
Figure 5:
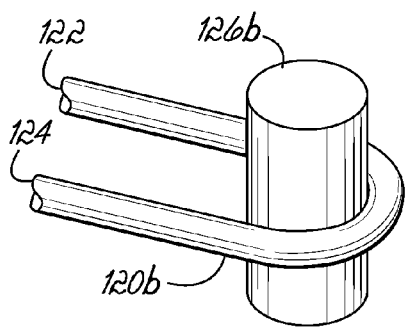
Figure 6:
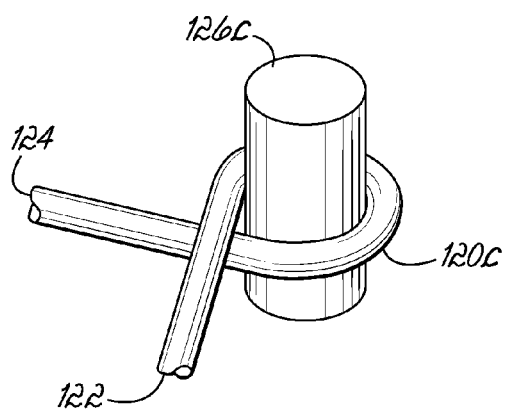
Figure 7:
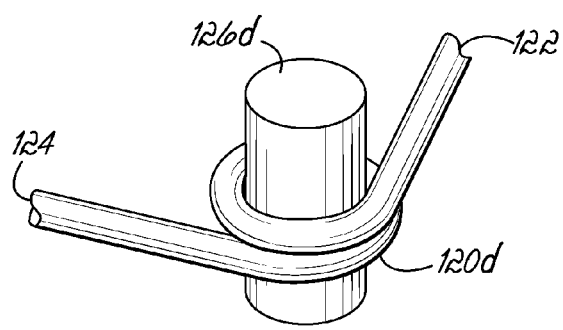

With respect to the embodiment that is shown in FIGS. 1 and 3, the mechanical capstan amplifier 40 in use with the biomimetic hand 10 includes control motor 44, 46, 48, 50 which are operably coupled to a control rod 100, 102, 104, 106 that is supported by a housing 108. Because multiple cords 36 are driven by the mechanical capstan amplifier 40, the control rods 100, 102, 104, 106 vary in height, or specifically as shown, decrease in height along the housing 108 to reduce the likelihood that the cords 36 become entangled during use. Each control rod 100, 102, 104, 106 may include a washer 110, as was describe previously with reference to FIG. 2.

An actuating end 112 of each cord 36 is coupled to the control rod 100, 102, 104, 106 so that operation of the control motors 44, 46, 48, 50 causes the cord 36 to wind around the control rod 100, 102, 104, 106. Each cord 36 also extends, at least partially, around a drive rod 114 having a washer 118, which is supported by the housing 108 and operably controlled by the large driving motor 42. Because each cord 36 is coupled to a control rod 100, 102, 104, 106 of varying height, the cords 36 contact the drive rod 114 along a different position of the drive rod 114. Though not shown, the drive rod may include a plurality of convex portions that receive and retain the cords 36 in their appropriate positions and to further reduce the likelihood of entanglement.

Because the load end 116 of each cord 36 is coupled to one of the knobs 34 positioned at the distal joints 28, tensioning one or more of the cords, by activating the appropriate control motor 44, 46, 48, and/or 50 causes the respective cord to tighten with respect to the drive motor 42, continued rotation of which creates a proximally-directed force on the distal phalanges 26 such that the selected fingers 14, 16, 18, and/or 20 extend distally away from the palm portion 12, such as in an open hand position. Accordingly, the cords 36, acting as muscle, pull the phalanges 22, 24, 26 in the desired direction.

Reversal of this movement includes reversing the tension on the respective cord. For example, the illustrative control motors 44, 46, 48, 50 may be reversed to release the tension at the drive rod 114. Additionally, while not specifically shown, another tensioning device, such as a spring or a counter-force mechanical capstan amplifier, may be used to contract the fingers back into a clutched first position. Thus, once the friction is released at the drive rod 114, the respective finger 14, 16, 18, 20 retracts into the rest, clenched state.

While the illustrative embodiments of the mechanical capstan amplifiers have included either one or four control rods and motors, it would be readily appreciated that other embodiments may be envisioned that incorporate any number of control rods and motors. Furthermore, one or more drive motors may be possible within the same housing so that two different muscular movements may be achieved.

Figure 8:
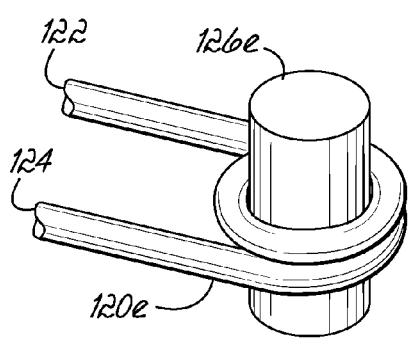

Referring now to FIGS. 4-8, additional configurations of cords relative to capstans are shown and described in greater detail. Specifically, each embodiment includes the cord (generally labeled with the reference numeral 120 and a variable subscript), having a load end 122 and an actuating end 124, and extending around a capstan (labeled with the reference numeral 126 and similar variable subscript) in accordance with varying angles of contact. The angles of contact are as follows: $\beta=270°$ (FIG. 4), $\beta=360°$ (FIG. 5), $\beta=450°$ (FIG. 6), $\beta=630°$ (FIGS. 7), and $\beta=720°$ (FIG. 8). The angle of contact is related to the response of the cord $120_n$ as tension is applied and the level of amplification that may be achieved by the capstan system. It would be readily appreciated that various other angles of contact are possible and the spirit of the invention should not be limited to the few specific examples provided herein.

As has been described in detail, a mechanical system has been described that is capable of producing the forces in a manner that is similar to biological muscle tissue. The mechanical capstan amplifier minimizes the mechanical system's weight, volume, and power consumption while providing a mechanism.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A mechanical capstan amplifier comprising:
a first tensioner;
a first actuating rod extending away from the first tensioner, the first tensioner configured to rotate the first actuating rod;
a second actuating rod positioned away from the first actuating rod;
a second tensioner coupled to the second actuating rod and configured to rotate the second actuating rod;
a drive motor;
a single drive rod extending away from the drive motor, the drive motor configured to rotate the single drive rod;
a first cord having a first end coupled to the first actuating rod and a second end coupled to a first load to be moved, wherein the first cord extends at least partially around the single drive rod; and
a second cord having a first end coupled to the second actuating rod and a second end coupled to a second load to be moved, wherein the second cord extends at least partially around the single drive rod at a position on the single drive rod that is different from a position of the first cord,
whereby actuation of the first tensioner causes the first cord to tighten around the single drive rod and moves the first load and actuation of the second tensioner causes the second cord to tighten around the single drive rod and moves the second load.

2. The mechanical capstan amplifier of claim 1, wherein the first and second loads are moved simultaneously.

3. The mechanical capstan amplifier of claim 1, wherein the first cord forms an angle of contact at the single drive rod between the first actuating rod and the first load, wherein the angle of contact is greater than about 180 degrees.

4. The mechanical capstan amplifier of claim 1 further comprising:
a housing supporting the first and second actuating rods, the first and second tensioners, the single drive rod, and the drive motor.

5. The mechanical capstan amplifier of claim 1, wherein the first and second loads are positioned away from the mechanical amplifier.

6. The mechanical capstan amplifier of claim 1, wherein the first tensioner and the second tensioner are spaced circumferentially about the drive motor.

7. The mechanical capstan amplifier of claim 1, wherein the first cord forms an angle of contact at the single drive rod between the first actuating rod and the first load, and the angle of contact is greater than or equal to about 270 degrees.

8. A biomimetic joint comprising:
a first skeletal element;
a second skeletal element rotationally coupled to the first skeletal element;
a third skeletal element positioned away from the first skeletal element and rotationally coupled to the second skeletal element; and
a mechanical capstan amplifier configured to move the first skeletal element and the third skeletal element with respect to the second skeletal element, the mechanical capstan amplifier comprising:
a first tensioner;
a first actuating rod extending away from the first tensioner, the first tensioner configured to rotate the first actuating rod;
a second tensioner;
a second actuating rod extending away from the second tensioner, the second tensioner configured to rotate the second actuating rod;
a drive motor;
a single drive rod extending away from the drive motor, the drive motor configured to rotate the single drive rod;
a first cord having a first end coupled to the first actuating rod and a second end coupled to the first skeletal element, wherein the first cord extends at least partially around the single drive rod; and
a second cord having a first end coupled to the second actuating rod and a second end coupled to the third skeletal element, wherein the second cord extends at least partially around the single drive rod at a position on the single drive rod that is different from a position of the first cord,
whereby actuation of the first tensioner causes the first cord to tighten around the single drive rod thereby causing the first skeletal element to rotate with respect to the second skeletal element, and actuation of the second tensioner causes the second cord to tighten around the single drive rod thereby causing the third skeletal element to rotate with respect to the second skeletal element.

9. The biomimetic joint of claim 8 further comprising:
a counter-force actuator extending between the first and second skeletal elements and configured to resist movement of the first skeletal element with respect to the second skeletal element.

10. The biomimetic joint of claim 9, wherein the counter-force actuator is a spring.

11. The biomimetic joint of claim 8, wherein the first tensioner and the second tensioner are spaced circumferentially about the drive motor.

12. The biomimetic joint of claim 8, wherein the first cord forms an angle of contact at the single drive rod between the first actuating rod and the first load, and the angle of contact is greater than or equal to about 270 degrees.

13. A method of moving a first load and a second load, the method comprising:
providing a first cord that extends at least partially around a single drive rod and to the first load;
providing a second cord that extends at least partially around the single drive rod and to the second load, the second cord at least partially surrounding the single drive rod at a position on the single drive rod that is different from a position of the first cord;
rotating the single drive rod while the first cord and the second cord are loosely coupled thereto; and
tightening the first cord and the second cord about the single drive rod such that continued rotation of the single drive rod creates friction between the single drive rod and the first cord and between the single drive rod and the second cord so that the first load and the second load are moved.

14. The method of claim 13 further comprising:
releasing the first cord such that the single drive rod rotates with the first cord loosely coupled thereto while the second cord remains tightened about the single drive rod and the second load continues to move.

15. The method of claim 13, wherein tightening the first cord and the second cord includes coupling the first cord to a first actuating rod and coupling the second cord to a second actuating rod and rotating the first actuating rod and the second actuating rod.

16. The method of claim 13, further comprising:
providing the first tensioner and the second tensioner in a circumferentially spaced configuration about the drive motor.

17. The method of claim 13, further comprising:
forming an angle of contact with the first cord at the single drive rod between the first actuating rod and the first load, wherein the angle of contact is greater than or equal to about 270 degrees.

* * * * *